US007943815B2

(12) United States Patent
Maggi et al.

(10) Patent No.: US 7,943,815 B2
(45) Date of Patent: May 17, 2011

(54) TRANSGENIC MOUSE FOR SCREENING AND FOR STUDIES OF THE PHARMACODYNAMICS AND PHARMACOKINETICS OF LIGANDS ACTING ON THE OESTROGEN RECEPTOR AND ITS INTRACELLULAR RECEPTORS, AND METHOD FOR THE PREPARATION THEREOF

(75) Inventors: Adriana Caterina Maggi, Milan (IT); Paolo Ciana, Gravellona Toce (IT)

(73) Assignee: T.O.P. (Transgenic Operative Products) S.R.L., Cascina Codazza (IT)

( * ) Notice: Subject to any disclaimer, the term of this patent is extended or adjusted under 35 U.S.C. 154(b) by 970 days.

(21) Appl. No.: 10/311,347

(22) PCT Filed: Jul. 2, 2001

(86) PCT No.: PCT/EP01/07622

§ 371 (c)(1),
(2), (4) Date: May 30, 2003

(87) PCT Pub. No.: WO02/01949

PCT Pub. Date: Jan. 10, 2002

(65) Prior Publication Data

US 2003/0182676 A1     Sep. 25, 2003

(30) Foreign Application Priority Data

Jul. 4, 2000 (IT) .............................. MI2000A1503

(51) Int. Cl.
*A01K 67/027* (2006.01)
*C12N 15/00* (2006.01)
*A01N 63/00* (2006.01)
*A61K 48/00* (2006.01)
*C07H 21/04* (2006.01)

(52) U.S. Cl. ...... 800/18; 800/25; 435/320.1; 424/93.21; 536/24.1

(58) Field of Classification Search .................. 800/18, 800/25; 435/320.1; 424/93.21; 536/24.1
See application file for complete search history.

(56) References Cited

U.S. PATENT DOCUMENTS 6,562,589 B1 * 5/2003 Meltzer et al. ............... 435/69.1

FOREIGN PATENT DOCUMENTS

WO    WO96/40911    12/1996

OTHER PUBLICATIONS

Ciana, P et al. Mol Endocrinology 15:1104-1113, 2001.*
Saceda, M et al. Endocrinology 137:4322-4330, 1996.*
Recillas-Targa, F et al. BioEassys 26:796-807, 2004.*
Hogan, B et al. Manipulating the Mouse Embryo. Cold Spring Harbor Laboratory Press, NY. pp. 157-182, 1986.*
Cameron, ER. Mol Biotech 7:253-265, 1997.*
Sigmund, CD. Art Thromb Vas Biol 20:1425-1429, 2000.*
Mullins, JJ and LJ Mullins. Hypertension 22:630-633, 1993.*
Neiman, H. Transgenic Research 7:73-75, 1998.*
Kappel, CA et al. Curr Opin Biotech 3:548-553, 1992.*
Houdebine, LM J Biotech 34:269-287, 1994.*
Wall, RJ. Theriogenology 45:57-68, 1996.*
Edwards et al., 2003, American Journal of Reproductive Immunology, vol. 50, p. 113-123.*
Dinnyes et al., 2008, Reproduction in Domestic Animals, vol. 43, suppl. 2, p. 302-309.*
Koo et al., 2001, Molecular reproduction and Development, vol. 58, p. 15-21.*
Houdebine, L-M., 2002, Journal of Biotechnology, vol. 98, p. 145-160.*
Kappel et al., 1992, Current Opinion in Biotechnology, vol. 3, p. 548-553.*
Wall, R. J., 1996, Theriogenology, vol. 45, p. 57-68.*
Sigmund, C., Jun. 2000, Arterioscler. Thromb. Vasc. Biol., p. 1425-1429.*
Montoliu et al., 1995, PNAS, vol. 92, pp. 4244-4248.*
Mcknight et al., 1996, Molecular Reproduction and Development, vol. 44, p. 179-184.*
Karperien et al, Mol Endo, 1999, pp. 1183-1196, Identification of a Retinoic Acid-Inducible Element in the Murine PTH/PTHrP . . . .
Solomin et al, Nature, vol. 395, Sep. 24, 1998, pp. 398-402, Retinoid-X receptor signalling in the developing spinal cord.
VanderKuur et al, Biochemistry, vol. 32, No. 27, 1993, pp. 7016-7021, Effects of Estradiol-17β Analogues on Activation . . . .
Arnold et al, Env Health Perspectives, vol. 104, No. 5, May 1996 pp. 544-548, A Yeast Estrogen Screen for Examining the . . . .
Klein-Hitpaβ et al, J Mol Biol, 201, 1988, pp. 537-544, Synergism of Closely Adjacent Estrogen-responsive Elements . . . .
Allen et al, Plant Mol Biol, 43, 2000, pp. 361-376, Use of matrix attachment regions (MARs) to minimize transgene silencing.
Sun et al, Cell, vol. 99, Nov. 24, 1999, pp. 459-462, Putting Boundaries on Silence.
Migliaccio et al, Endocrinology, vol. 130, No. 5, 1992, pp. 2617-2624, Estrogens Modulate the Responsiveness of . . . .
Pikaart et al, Genes & Dev, 12, 1998, pp. 2852-2862, Loss of transcriptional activity of a transgene is accompanied by DNA . . . .
Wang et al, Nature Biotech, vol. 15, Mar. 1997, pp. 239-243, Ligand-inducible and liver-specific target gene expression . . . .
Costantini et al, Nature, vol. 294, Nov. 5, 1981, pp. 92-94, Introduction of a rabbit β-globin gene into the mouse germ line.
Chalfie et al, Science, vol. 263, Feb. 11, 1994, pp. 802-805, Green Fluorescent Protein as a Marker for Gene Expression.
Chung et al, Cell, vol. 74, Aug. 13, 1993, pp. 505-513, A 5' Element of the Chicken β-Globin Domain Serves as an Insulator in . . . .
de The et al, Nature, vol. 343, Jan. 11, 1990, Identification of a retinoic acid responsive element in the retinoic acid . . . .

(Continued)

*Primary Examiner* — Shin-Lin Chen
(74) *Attorney, Agent, or Firm* — Jacobson Holman PLLC

(57) ABSTRACT

The object of the invention is a method for the production of a non-human transgenic mammal by means of which it is possible to monitor in vivo and in all the tissues the state of activation of any intracellular receptor, utilizing a reporter gene inducible by natural or synthetic molecules which modulate the activity of such receptor. The mammal is question is preferably a mouse.

9 Claims, 8 Drawing Sheets

OTHER PUBLICATIONS

De Wet et al, Mol & Cell Biology, vol. 7, No. 2, Feb. 1987, pp. 725-737, Firefly Luciferase. Gene: Structure and Expression in . . . .
Durand et al, Cell, vol. 71, Oct. 2, 1992, pp. 73-85, All-Trans and 9-Cis Retinoic Acid Induction of CRABPII Transcription is . . . .
Fu et al, Nature Biotechnology, Vo.. 16, Mar. 1998, pp. 253-257, Viral sequences enable efficient and tissue-specific . . . .
Science, vol. 214, Dec. 11, 1981, pp. 1244-1246, Integration and Stable Germ Line Transmission of Genes Injected into Mouse . . . .
Gorman et al, Mol & Cell, vol. 2, No. 9, Sep. 1982, Recombinant Genomes Which Express Chloramphenicol Acetyltransferase in . . . .
Gossler et al, Proc Natl Acad Sci, vol. 83, Dec. 1986, pp. 9065-9069, Transgenesis by means of blastocyst-derived . . . .
Klein-Hitpaβ et al, Cell, vol. 46, Sep. 26, 1986, pp. 1053-1061, An Estrogen-Responsive Element Derived from the 5' Flanking . . . .
Kliewer et al, Nature, vol. 358, Aug. 27, 1992, pp. 771-774, Convergence of 9-cis retinoic acid and peroxisome proliferator . . . .
Nucleic Acids Research, vol. 15, No. 13, 1987, p. 5490, CAT constructions with multiple unique restriction sites for the . . . .
Molecular Cloning A Laboratory Manual, Second Edition, Preparation and Examination of Agarose Gels.
Nilsson et al, Breast Cancer Res 2, 2000, pp. 360-366, Estrogen receptor transcription and transactivation Basic aspects of . . . .
Noda et al, Proc Natl Acad Sci, 87, 1990, pp. 9995-9999, Identification of a DNA sequence responsible for binding of . . . .
Robertson et al, Nature, vol. 323, Oct. 2, 1986, Germ-line transmission of genes introduced into cultured pluripoential cells . . . .
Sap et al, EMBO Journal 9, 1990, pp. 887-896, A major thyroid hormone response element in the third intron of the rat . . . .
Sharpe et al, The Lancet, vol. 341, May 29, 1993, Are oestrogens involved in falling sperm counts and disorders of the male . . . .
Stief et al, Nature, vol. 341, Sep. 28, 1989, A nuclear DNA attachment element mediates elevated and position-independent gene activity.
Stunnenberg, Bioessays 15, 1993, pp. 309-315, Mechanisms of Transactivation by Retinoic Acid Receptors.
Twai et al, Annu Rev Biochem 63, 1994, pp. 451-486, Molecular Mechanisms of Action of Steroid/Thyroid Receptor Superfamily . . . .
Won der Ahe et al, nature, vol. 313, 1985, pp. 706-709, Glucocorticoid and progesterone receptors bind to the same sites . . . .
Lokarnik et al, Science, vol. 279, Jan. 2, 1998, pp. 84-88, Quantitation of Transcription and Clonal Selection of Single Living . . . .

* cited by examiner

Starting construct containing the TK (-109) promoter.

Ligation of the multimerized ERE sequences upstream the promoter region.

Final constructs - Ligation of the MAR and HS4 sequences in the flanking regions of the pERE2XTKluc construct.

EcoRI/EcoRI 0.77 Kb probe used for the screening of transgenic mice generated with pMAR and pHS4 constructs.

Luciferase activity in line 2 of transgenic mice.

Luciferase activity in line 61.

Luciferase activity in line 59 of transgenic mice.

Pharmacological modulation of luciferase activity *in vivo*. Luciferase activity in bone and liver protein extracts of two months old male mice.

Upper panel: time course of luciferase activity in liver and bone of transgenic mice treated with 17β-estradiol (E2). Lower panel: tissue distribution of the E2-dependent luciferase induction within several tissues.

Expression of luciferase in primary bone marrow cells from transgenic mice.

SEQUENCE LISTING

```
<160> NUMBER OF SEQ ID NOS: 10

<210> SEQ ID NO 1
<211> LENGTH: 13
<212> TYPE: DNA
<213> ORGANISM: Artificial Sequence
<220> FEATURE:
<221> NAME/KEY: misc_feature
<222> LOCATION: [6]..[8]
<223> OTHER INFORMATION: Synthesized; "n" at locations [6] through [8]
      can be any base

<400> SEQUENCE: 1
ggtcannntg acc                                                          13
```

```
<210> SEQ ID NO 2
<211> LENGTH: 15
<212> TYPE: DNA
<213> ORGANISM: Artificial Sequence
<220> FEATURE:
<221> NAME/KEY: misc_feature
<222> LOCATION: [7]..[9]
<223> OTHER INFORMATION: Synthesized; "n" at locations [7] through [9]
      can be any base

<400> SEQUENCE: 2
agaacannnt gttct                                                          15

<210> SEQ ID NO 3
<211> LENGTH: 17
<212> TYPE: DNA
<213> ORGANISM: Artificial Sequence
<220> FEATURE:
<221> NAME/KEY: misc_feature
<222> LOCATION: [7]..[11]
<223> OTHER INFORMATION: Synthesized; "n" at locations [7] through [11]
      can be any base

<400> SEQUENCE: 3
ggttcannnn nagttca                                                        17

<210> SEQ ID NO 4
<211> LENGTH: 14
<212> TYPE: DNA
<213> ORGANISM: Artificial Sequence
<220> FEATURE:
<221> NAME/KEY: misc_feature
<222> LOCATION: [7]..[8]
<223> OTHER INFORMATION: Synthesized; "n" at locations [7] through [8]
      can be any base

<400> SEQUENCE: 4
agttcannag gtca                                                           14

<210> SEQ ID NO 5
<211> LENGTH: 13
<212> TYPE: DNA
<213> ORGANISM: Artificial Sequence
<220> FEATURE:
<221> NAME/KEY: misc_feature
<222> LOCATION: [7]..[7]
<223> OTHER INFORMATION: Synthesized; "n" at locations [7] through [7]
      can be any base

<400> SEQUENCE: 5
agttcanagg tca                                                            13

<210> SEQ ID NO 6
<211> LENGTH: 16
<212> TYPE: DNA
<213> ORGANISM: Artificial Sequence
<220> FEATURE:
<221> NAME/KEY: misc_feature
<222> LOCATION: [7]..[10]
<223> OTHER INFORMATION: Synthesized; "n" at locations [7] through [10]
      can be any base

<400> SEQUENCE: 6
gggtcannnn aggtcc                                                         16

<210> SEQ ID NO 7
<211> LENGTH: 14
<212> TYPE: DNA
<213> ORGANISM: Artificial Sequence
```

```
<220> FEATURE:
<221> NAME/KEY: misc_feature
<222> LOCATION: [6]..[8]
<223> OTHER INFORMATION: Synthesized; "n" at locations [6] through [8]
      can be any base

<400> SEQUENCE: 7
gttcannngg ttca                                                          14

<210> SEQ ID NO 8
<211> LENGTH: 13
<212> TYPE: DNA
<213> ORGANISM: Artificial Sequence
<220> FEATURE:
<221> NAME/KEY: misc_feature
<222> LOCATION: [7]..[7]
<223> OTHER INFORMATION: Synthesized; "n" at locations [7] through [7]
      can be any base

<400> SEQUENCE: 8
aggtcanagg tca                                                           13

<210> SEQ ID NO 9
<211> LENGTH: 10776
<212> TYPE: DNA
<213> ORGANISM: Artificial sequence
<220> FEATURE:
<223> OTHER INFORMATION: Synthesized

<400> SEQUENCE: 9
```

| | | | | | |
|---|---|---|---|---|---|
| cggtggagct | ccaattcgcc | ctatagtgag | tcgtattacg | cgcgctcact | ggccgtcgtt    60 |
| ttacaacgtc | gtgactggga | aaaccctggc | gttacccaac | ttaatcgcct | tgcagcacat   120 |
| cccccttcg  | ccagctggcg | taatagcgaa | gaggcccgca | ccgatcgccc | ttcccaacag   180 |
| ttgcgcagcc | tgaatggcga | atggaaattg | taagcgttaa | tattttgtta | aaattcgcgt   240 |
| taaattttg  | ttaaatcagc | tcatttttta | accaataggc | cgaaatcggc | aaaatccctt   300 |
| ataaatcaaa | agaatagacc | gagatagggt | tgagtgttgt | tccagtttgg | aacaagagtc   360 |
| cactattaaa | gaacgtggac | tccaacgtca | aagggcgaaa | aaccgtctat | cagggcgatg   420 |
| gcccactacg | tgaaccatca | ccctaatcaa | gttttttggg | gtcgaggtgc | cgtaaagcac   480 |
| taaatcggaa | ccctaaaggg | agcccccgat | ttagagcttg | acggggaaag | ccggcgaacg   540 |
| tggcgagaaa | ggaagggaag | aaagcgaaag | gagcgggcgc | tagggcgctg | gcaagtgtag   600 |
| cggtcacgct | gcgcgtaacc | accacacccg | ccgcgcttaa | tgcgccgcta | cagggcgcgt   660 |
| cagtggcact | tttcggggaa | atgtgcgcgg | aacccctatt | tgtttatttt | tctaaataca   720 |
| ttcaaatatg | tatccgctca | tgagacaata | accctgataa | atgcttcaat | aatattgaaa   780 |
| aaggaagagt | atgagtattc | aacatttccg | tgtcgccctt | attcccttt  | ttgcggcatt   840 |
| ttgccttcct | gtttttgctc | acccagaaac | gctggtgaaa | gtaaaagatg | ctgaagatca   900 |
| gttgggtgca | cgagtgggtt | acatcgaact | ggatctcaac | agcggtaaga | tccttgagag   960 |
| ttttcgcccc | gaagaacgtt | ttccaatgat | gagcactttt | aaagttctgc | tatgtggcgc  1020 |
| ggtattatcc | cgtattgacg | ccgggcaaga | gcaactcggt | cgccgcatac | actattctca  1080 |
| gaatgacttg | gttgagtact | caccagtcac | agaaaagcat | cttacggatg | gcatgacagt  1140 |
| aagagaatta | tgcagtgctg | ccataaccat | gagtgataac | actgcggcca | acttacttct  1200 |
| gacaacgatc | ggaggaccga | aggagctaac | cgctttttg  | cacaacatgg | gggatcatgt  1260 |
| aactcgcctt | gatcgttggg | aaccggagct | gaatgaagcc | ataccaaacg | acgagcgtga  1320 |
| caccacgatg | cctgtagcaa | tggcaacaac | gttgcgcaaa | ctattaactg | gcgaactact  1380 |

```
tactctagct tcccggcaac aattaataga ctggatggag gcggataaag ttgcaggacc   1440
acttctgcgc tcggcccttc cggctggctg gtttattgct gataaatctg gagccggtga   1500
gcgtgggtct cgcggtatca ttgcagcact ggggccagat ggtaagccct cccgtatcgt   1560
agttatctac acgacgggga gtcaggcaac tatggatgaa cgaaatagac agatcgctga   1620
gataggtgcc tcactgatta agcattggta actgtcagac caagtttact catatatact   1680
ttagattgat ttaaaacttc attttttaatt taaaaggatc taggtgaaga tcctttttga   1740
taatctcatg accaaaatcc cttaacgtga gttttcgttc cactgagcgt cagaccccgt   1800
agaaaagatc aaaggatctt cttgagatcc ttttttttctg cgcgtaatct gctgcttgca   1860
aacaaaaaaa ccaccgctac cagcggtggt ttgtttgccg gatcaagagc taccaactct   1920
ttttccgaag gtaactggct tcagcagagc gcagatacca atactgtcc ttctagtgta   1980 gccgtagtta ggccaccact tcaagaactc tgtagcaccg cctacatacc tcgctctgct   2040
aatcctgtta ccagtggctg ctgccagtgg cgataagtcg tgtcttaccg ggttggactc   2100
aagacgatag ttaccggata aggcgcagcg gtcgggctga acggggggtt cgtgcacaca   2160
gcccagcttg gagcgaacga cctacaccga actgagatac ctacagcgtg agctatgaga   2220
aagcgccacg cttcccgaag ggagaaaggc ggacaggtat ccggtaagcg cagggtcgg   2280 aacaggagag cgcacgaggg agcttccagg gggaaacgcc tggtatcttt atagtcctgt   2340
cgggtttcgc cacctctgac ttgagcgtcg attttttgtga tgctcgtcag ggggggcggag   2400 cctatggaaa aacgccagca acgcggcctt tttacggttc ctggccttttt gctggccttt   2460 tgctcacatg ttctttcctg cgttatcccc tgattctgtg ataaccgta ttaccgcctt   2520 tgagtgagct gataccgctc gccgcagccg aacgaccgag cgcagcgagt cagtgagcga   2580
ggaagcggaa gagcgcccaa tacgcaaacc gcctctcccc gcgcgttggc cgattcatta   2640
atgcagctgg cacgacaggt ttcccgactg gaaagcgggc agtgagcgca acgcaattaa   2700
tgtgagttag ctcactcatt aggcacccca ggctttacac tttatgcttc cggctcgtat   2760
gttgtgtgga attgtgagcg gataacaatt tcacacagga aacagctatg accatgatta   2820
cgccaagcgc gcaattaacc ctcactaaag ggaacaaaag ctgtcgactc tagagggaca   2880 gcccccccc aaagccccca gggatgtaat tacgtccctc cccgctaggg gggcagcagc   2940
gagccgcccg gggctccgct ccggtccggc gctcccccg catccccgag ccggcagcgt   3000
gcggggacag cccgggcacg gggaaggtgg cacgggatcg ctttcctctg aacgcttctc   3060
gctgctcttt gagcctgcag acacctgggg gatacgggga aaaagcttta ggctgaaaga   3120
gagatttaga atgacagaat catagaacgc ctgggttgca aaggagcaca gtgctcatcc   3180
agatccaacc ccctgctatg tgcaggtcat caaccagcag cccagcgcgt cagagccaca   3240
tccagcctgg ccttgaatgc ctgcctgcag ggatggggca tccacagcct ccttgggcaa   3300
cctgttcagt gcgtcaccac cctctgggga aaaactgcct cctcatatcc aacccaaacc   3360
tcccctgtct cagtgtaaag ccattccccc ttgtcctatc aaggggggagt ttgctgtgac   3420 attgttggtc tggggtgaca catgtttgcc aattcagtgc tcacggagag gcagatcttg   3480
ggataaggaa gtcaggaca gcatggacgt ggacatgcag gtgttgaggc tctggacact   3540
ccaagtcaca gcgttcagaa cagccttaag gtcaagaaga taggatagaa ggacaaagag   3600
caagttaaaa cccagcatgg agaggagcac aaaaaggcca cagacactgc tggtccctgt   3660
gtctgagcct gcatgtttga tggtgtctgg atgcaagcag aaggggtgga agagcttgcc   3720
tggagagata caggctgggt cgtaggactg ggacaggcag ctggagaatt gccatgtaga   3780
```

```
tgttcataca atcgtcaaat catgaaggct ggaaaagctc caagatcccc aagaccaacc    3840
ccaacccacc caccgtgcca ctggccatgt ccctcagtgc cacatcccca cagttcttca    3900
tcacctccag ggacggtgac cccctcctcc gtggcagctg tgccactgca gcaccgctct    3960
ttggagaagg taaatcttgc taaatccagc ccgaccctcc cctggcacaa cgtaaggcca    4020
ttatctctca tccaactcca ggacggagtc agtgagaata tttctagaga gctcacgggg    4080 acagccccc cccaaagccc caggggatgt aattacgtcc ctcccccgct aggggcagc     4140 agcgagccgc ccggggctcc gctccggtcc ggcgctcccc ccgcatcccc gagccggcag    4200
cgtgcgggga cagcccgggc acggggaagg tggcacggga tcgctttcct ctgaacgctt    4260
ctcgctgctc tttgagcctg cagacacctg ggggatacgg ggaaaaagct taggctgaa    4320 agagagattt agaatgacag aatcatagaa cgcctgggtt gcaaggagc acagtgctca     4380 tccagatcca accccctgct atgtgcaggt catcaaccag cagcccagcg cgtcagagcc    4440
acatccagcc tggccttgaa tgcctgcctg cagggatggg gcatccacag cctccttggg    4500
caacctgttc agtgcgtcac caccctctgg ggaaaaactg cctcctcata tccaacccaa    4560
acctcccctg tctcagtgta aagccattcc cccttgtcct atcaagggg agtttgctgt      4620 gacattgttg gtctggggtg acacatgttt gccaattcag tgctcacgga gaggcagatc    4680
ttgggataag gaagtgcagg acagcatgga cgtggacatg caggtgttga ggctctggac    4740
actccaagtc acagcgttca gaacagcctt aaggtcaaga agataggata gaaggacaaa    4800
gagcaagtta aaacccagca tggagaggag cacaaaaagg ccacagacac tgctggtccc    4860
tgtgtctgag cctgcatgtt tgatggtgtc tggatgcaag cagaaggggt ggaagagctt    4920
gcctggagag atacaggctg ggtcgtagga ctgggacagg cagctggaga attgccatgt    4980
agatgttcat acaatcgtca aatcatgaag gctggaaaag ctccaagatc cccaagacca    5040
accccaaccc acccaccgtg ccactggcca tgtccctcag tgccacatcc ccacagttct    5100
tcatcacctc cagggacggt gaccccctcc tccgtggcag ctgtgccact gcagcaccgc    5160 tcttggaga aggtaaatct tgctaaatcc agcccgaccc tcccctggca caacgtaagg     5220
ccattatctc tcatccaact ccaggacgga gtcagtgaga atattggcct ctagaggatc    5280
caagcttatc gatgaattca ccgttctaga ttaattaagt cagggggccc cctcgaggtc    5340
gatcgagatc tagcctgact gcggatccgc aggtcactgt gacctagatc cgcaggtcac    5400
tgtgacctac atctgatatc atcgtcgacg gtatcgataa gcttcgaccg atccggcccc    5460
gcccagcgtc ttgtcattgg cgaattcgaa cacgcagatg cagtcgggc ggcgcggtcc     5520 gaggtccact tcgcatatta aggtgacgcg tgtggcctcg aacaccgagc gaccctgcag    5580
cgacccgctt aacagcgtca acagcgtgcc gcagatctcg agagatctcg aggcatgcaa    5640
gcttggcatt ccggtactgt tggtaaaatg gaagacgcca aaaacataaa gaaaggcccg    5700
gcgccattct atcctctaga ggatggaacc gctggagagc aactgcataa ggctatgaag    5760
agatacgccc tggttcctgg aacaattgct tttacagatg cacatatcga ggtgaacatc    5820
acgtacgcgg aatacttcga atgtccgtt cggttggcag aagctatgaa acgatatggg     5880
ctgaatacaa atcacagaat cgtcgtatgc agtgaaaact ctcttcaatt ctttatgccg    5940
gtgttgggcg cgttatttat cggagttgca gttgcgcccg cgaacgacat ttataatgaa    6000
cgtgaattgc tcaacagtat gaacatttcg cagcctaccg tagtgtttgt ttccaaaaag    6060 ggggttgcaaa aaatttttgaa cgtgcaaaaa aaattaccaa taatccagaa aattattatc    6120
atggattcta aaacggatta ccagggattt cagtcgatgt acacgttcgt cacatctcat    6180
```

```
ctacctcccg gttttaatga atacgatttt gtaccagagt cctttgatcg tgacaaaaca    6240
attgcactga taatgaattc ctctggatct actgggttac ctaagggtgt ggcccttccg    6300
catagaactg cctgcgtcag attctcgcat gccagagatc ctattttttgg caatcaaatc   6360 attccggata ctgcgatttt aagtgttgtt ccattccatc acggttttgg aatgtttact    6420
acactcggat atttgatatg tggatttcga gtcgtcttaa tgtatagatt tgaagaagag    6480
ctgtttttac gatcccttca ggattacaaa attcaaagtg cgttgctagt accaacccta    6540
ttttcattct tcgccaaaag cactctgatt gacaaatacg atttatctaa tttacacgaa    6600
attgcttctg ggggcgcacc tctttcgaaa gaagtcgggg aagcggttgc aaaacgcttc    6660
catcttccag ggatacgaca aggatatggg ctcactgaga ctacatcagc tattctgatt    6720
acacccgagg gggatgataa accgggcgcg gtcggtaaag ttgttccatt ttttgaagcg    6780
aaggttgtgg atctggatac cgggaaaacg ctgggcgtta atcagagagg cgaattatgt    6840
gtcagaggac ctatgattat gtccggttat gtaaacaatc cggaagcgac caacgccttg    6900
attgacaagg atggatggct acattctgga gacatagctt actgggacga agacgaacac    6960
ttcttcatag ttgaccgctt gaagtcttta attaaataca aaggatatca ggtggccccc    7020
gctgaattgg aatcgatatt gttacaacac cccaacatct tcgacgcggg cgtggcaggt    7080
cttcccgacg atgacgccgg tgaacttccc gccgccgttg ttgttttgga gcacggaaag    7140
acgatgacgg aaaagagat cgtggattac gtggccagtc aagtaacaac cgcgaaaaag    7200
ttgcgcggag gagttgtgtt tgtggacgaa gtaccgaaag gtcttaccgg aaaactcgac    7260
gcaagaaaaa tcagagagat cctcataaag gccaagaagg gcggaaagtc caaattgtaa    7320
aatgtaactg tattcagcga tgacgaaatt cttagctatt gtaatactgc gatgagtggc    7380
agggcggggc gtaattttttt taaggcagtt attggtgccc ttaaacgcct ggtgctacgc    7440
ctgaataagt gataataagc ggatgaatgg cagaaattcg ccggatcttt gtgaaggaac    7500
cttacttctg tggtgtgaca taattggaca aactacctac agagatttaa agctctaagg    7560
taaatataaa attttaaagt gtataatgtg ttaaactact gattctaatt gtttgtgtat    7620
tttagattcc aacctatgga actgatgaat gggagcagtg gtggaatgcc tttaatgagg    7680
aaaacctgtt tgctcagaa gaaatgccat ctagtgatga tgaggctact gctgactctc    7740
aacattctac tcctccaaaa aagaagagaa aggtagaaga ccccaaggac tttccttcag    7800
aattgctaag ttttttgagt catgctgtgt ttagtaatag aactcttgct tgctttgcta    7860
tttacaccac aaaggaaaaa gctgcactgc tatacaagaa aattatggaa aaatattctg    7920 taaccttat aagtaggcat aacagttata atcataacat actgttttttt cttactccac    7980 acaggcatag agtgtctgct attaataact atgctcaaaa attgtgtacc tttagctttt    8040
taatttgtaa agggggttaat aaggaatatt tgatgtatag tgccttgact agagatcata    8100
atcagccata ccacatttgt agaggtttta cttgctttaa aaaacctccc acacctcccc    8160
ctgaacctga acataaaat gaatgcaatt gttgttgtta acttgtttat tgcagcttat    8220
aatggttaca aataaagcaa tagcatcaca aatttcacaa ataaagcatt ttttcactg    8280 cattctagtt gtggttttgtc caaactcatc aatgtatctt attcatgtct ggatccgtcg    8340 aggggggatcc actagttcta gagcggccgc caccgtcgac tctagaggga cagcccccc    8400 ccaaagcccc cagggatgta attacgtccc tcccccgcta gggggcagca gcgagccgcc    8460
cggggctccg ctccggtccg gcgctccccc cgcatcccg agccgcagc gtgcgggac    8520 agcccgggca cggggaaggt ggcacgggat cgctttcctc tgaacgcttc tcgctgctct    8580
```

```
ttgagcctgc agacacctgg gggatacggg gaaaaagctt taggctgaaa gagagattta    8640
gaatgacaga atcatagaac gcctgggttg caaaggagca cagtgctcat ccagatccaa    8700
cccctgcta tgtgcaggtc atcaaccagc agcccagcgc gtcagagcca catccagcct    8760
ggccttgaat gcctgcctgc agggatgggg catccacagc ctccttgggc aacctgttca    8820
gtgcgtcacc accctctggg gaaaaactgc ctcctcatat ccaacccaaa cctcccctgt    8880
ctcagtgtaa agccattccc ccttgtccta tcaaggggga gtttgctgtg acattgttgg    8940
tctggggtga cacatgtttg ccaattcagt gctcacggag aggcagatct tgggataagg    9000
aagtgcagga cagcatggac gtggacatgc aggtgttgag gctctggaca ctccaagtca    9060
cagcgttcag aacagcctta aggtcaagaa gataggatag aaggacaaag agcaagttaa    9120
aacccagcat ggagaggagc acaaaaaggc cacagacact gctggtccct gtgtctgagc    9180
ctgcatgttt gatggtgtct ggatgcaagc agaaggggtg gaagagcttg cctggagaga    9240
tacaggctgg gtcgtaggac tgggacaggc agctggagaa ttgccatgta gatgttcata    9300
caatcgtcaa atcatgaagg ctggaaaagc tccaagatcc caagaccaa ccccaaccca    9360
cccaccgtgc cactggccat gtccctcagt gccacatccc cacagttctt catcacctcc    9420
agggacggtg accccctcct ccgtggcagc tgtgccactg cagcaccgct ctttggagaa    9480
ggtaaatctt gctaaatcca gcccgaccct cccctggcac aacgtaaggc cattatctct    9540
catccaactc caggacggag tcagtgagaa tatttctaga gagctcacgg ggacagcccc    9600
cccccaaagc ccccagggat gtaattacgt ccctcccccg ctaggggca gcagcgagcc    9660
gcccggggct ccgctccggt ccggcgctcc ccccgcatcc ccgagccggc agcgtgcggg    9720
gacagcccgg gcacgggaa ggtggcacgg gatcgctttc ctctgaacgc ttctcgctgc    9780
tctttgagcc tgcagacacc tgggggatac ggggaaaaag ctttaggctg aaagagagat    9840
ttagaatgac agaatcatag aacgcctggg ttgcaaagga gcacagtgct catccagatc    9900
caaccccctg ctatgtgcag gtcatcaacc agcagcccag cgcgtcagag ccacatccag    9960
cctggccttg aatgcctgcc tgcagggatg gggcatccac agcctccttg gcaacctgt    10020
tcagtgcgtc accaccctct ggggaaaaac tgcctcctca tatccaaccc aaacctcccc    10080
tgtctcagtg taaagccatt ccccttgtc ctatcaaggg ggagtttgct gtgacattgt    10140
tggtctgggg tgacacatgt tgccaattc agtgctcacg gagaggcaga tcttgggata    10200
aggaagtgca ggacagcatg gacgtggaca tgcaggtgtt gaggctctgg acactccaag    10260
tcacagcgtt cagaacagcc ttaaggtcaa gaagatagga tagaaggaca agagcaagt    10320
taaaacccag catggagagg agcacaaaaa ggccacagac actgctggtc cctgtgtctg    10380
agcctgcatg tttgatggtg tctggatgca agcagaaggg gtggaagagc ttgcctggag    10440
agatacaggc tgggtcgtag gactgggaca ggcagctgga gaattgccat gtagatgttc    10500
atacaatcgt caaatcatga aggctggaaa agctccaaga tccccaagac caaccccaac    10560
ccacccaccg tgccactggc catgtccctc agtgccacat ccccacagtt cttcatcacc    10620
tccagggacg gtgacccct cctccgtggc agctgtgcca ctgcagcacc gctctttgga    10680
gaaggtaaat cttgctaaat ccagcccgac cctcccctgg cacaacgtaa ggccattatc    10740
tctcatccaa ctccaggacg gagtcagtga gaatat                              10776
```

<210> SEQ ID NO 10
<211> LENGTH: 11837
<212> TYPE: DNA
<213> ORGANISM: Artificial sequence
<220> FEATURE:
<223> OTHER INFORMATION: Synthesized

<400> SEQUENCE: 10

```
gtggcactttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tccctttttt gcggcatttt     180
gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacggatggc atgacagtaa     480
gagaattatg cagtgctgcc ataaccatga gtgataacac tgcggccaac ttacttctga     540
caacgatcgg aggaccgaag gagctaaccg cttttttgca caacatgggg gatcatgtaa     600
ctcgccttga tcgttgggaa ccggagctga tgaagccat accaaacgac gagcgtgaca     660
ccacgatgcc tgtagcaatg gcaacaacgt tgcgcaaact attaactggc gaactactta     720
ctctagcttc ccggcaacaa ttaatagact ggatggaggc ggataaagtt gcaggaccac     780
ttctgcgctc ggcccttccg gctggctggt ttattgctga taaatctgga gccggtgagc     840
gtgggtctcg cggtatcatt gcagcactgg ggccagatgg taagccctcc cgtatcgtag     900
ttatctacac gacggggagt caggcaacta tggatgaacg aaatagacag atcgctgaga     960
taggtgcctc actgattaag cattggtaac tgtcagacca agtttactca tatatacttt    1020
agattgattt aaaacttcat ttttaattta aaaggatcta ggtgaagatc cttttgata    1080 atctcatgac caaaatccct taacgtgagt tttcgttcca ctgagcgtca gaccccgtag    1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatgaaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct gggatccata atataactgt    2220
accaggtttt ggtttattac atgtgactga cggcttccta tgcgtgctca gaaaacggca    2280
```

-continued

```
gttgggcact gcactgcccg gtgatggtgc cacggtggct cctgccgcct tctttgatat    2340
tcactctgtt gtatttcatc tcttgttgcc gatgaaagga tataacagtc tctgaggaaa    2400
tacttggtat ttcttctgat cagcgttttt ataagtaatg ttgaatattg gataaggctg    2460
tgtgtccttt gtcttgggag acaaagccca cagcaggtgg tggttgggtg gtggcagctc    2520
agtgacagga gaggtttttt tgcctgtttt ttttgttgtt ttttttttt aagtaaggtg     2580 ttcttttttc ttagtaaaat ttctactgga ctgtatgttt tgacaggtca gaaacatttc    2640
ttcaaaagaa gaacctttg gaaactgtac agccctttc tttcattccc ttttgctttt      2700
ctgtgccaat gcctttggtt ctgattgcat tatggaaaac gttgatcgga acttgaggtt    2760
tttatttata gtgtggcttg aaagcttgga tagctgttgt tacatgagat accttattaa    2820
gtttaggcca gcttgatgct ttattttttt tcctttgaag tagtgagcgt tctctggttt    2880
ttttcctttg aaactggcga ggcttagatt tttctaatgg gattttttac ctgatgatct    2940
agttgcatac ccaaatgctt gtaaatgttt tcctagttaa catgttgata acttcggatt    3000
tacatgttgt atatacttgt catctgtgtt tctagtaaaa atatatggca tttatagaaa    3060
tacgtaattc ctgatttcct ttttttttta tctctatgct ctgtgtgtac aggtcaaaca    3120
gacttcactc ctattttat ttatagaatt ttatatgcag tctgtcgttg gttcttgtgt     3180
tgtaaggata cagccttaaa tttcctagag cgatgctcag taaggcgggt tgtcacatgg    3240
gttcaaatgt aaaacgggca cgtttgctgc tgccttccca gatccaggac actaaactgc    3300
ttctgcaact gaggtataaa tcgcttcaga tcccaggaag tgtagatcca cgtgcatatt    3360
cttaaagaag aatgaatact ttctaaaata tgttggcata ggaagcaagc tgcatggatt    3420
tatttgggac ttaaattatt ttggtaacgg agtgcatagg ttttaaacac agttgcagca    3480
tgctaacgag tcacagcatt tatgcagaag tgatgcctgt tgcagctgtt tacggcactg    3540
ccttgcagtg agcattgcag ataggggtgg ggtgctttgt gtcgtgttgg gacacgctgc    3600
cacacagcca cctcccgaac atatctcacc tgctgggtac ttttcaaacc atcttagcag    3660
tagtagatga gttactatga aacagagaag ttcctcagtt ggatattctc atgggatgtc    3720
ttttttccca tgttgggcaa agtatgataa agcatctcta tttgtaaatt atgcacttgt    3780
tagttcctga atccttcta tagcaccact tattgcagca ggtgtaggct ctggtgtggc     3840
ctgtgtctgt gcttcaatct tttaagcttc tttggaaata cactgacttg attgaagtct    3900
cttgaagata gtaaacagta cttacctttg atcccaatga aatcgagcat ttcagttgta    3960
aaagaattcc gcctattcat accatgtaat gtaattttac accccagtg ctgacactt      4020 ggaatatatt caagtaatag actttggcct caccctcttg tgtactgtat tttgtaatag    4080
aaaatatttt aaactgtgca tatgattatt acattatgaa agagacattc tgctgatctt    4140
caaatgtaag aaaatgagga gtgcgtgtgc ttttataaat acaagtgatt gcaaattagt    4200
gcaggtgtcc ttaaaaaaaa aaaaaaaaag taatataaaa aggaccaggt gttttacaag    4260
tgaaatacat tcctatttgg taaacagtta cattttatg aagattacca gcgctgctga     4320
ctttctaaac ataaggctgt attgtcttcc tgtaccattg catttcctca ttcccaattt    4380
gcacaaggat gtctgggtaa actattcaag aaatggcttt gaaatacagc atgggagctt    4440
gtctgagttg gaatgcagag ttgcactgca aaatgtcagg aaatggatgt ctctcagaat    4500
gcccaactcc aaaggatttt atatgtgtat atagtaagca gtttcctgat tccagcaggc    4560
caagagtctg ctgaatgttg cgttgccgga gacctgtatt tctcaacaag gtaagatggt    4620
atcctagcaa ctgcggattt taatacattt tcagcagaag tacttagtta atctctacct    4680
```

```
ttagggatcg tttcatcatt tttagatgtt atacttgaaa tactgcataa cttttagctt      4740
tcatggcttc ctttttttca gcctttagga gactgttaag caatttgctg tccaacttt      4800 gtgttggtct taaactgcaa tagtagttta ccttgtattg aagaaataaa gaccattttt     4860
atattaaaaa atacttttgt ctgtcttcat tttgacttgt ctgatatcct tgcagtgctc      4920
attatgtcag ttctgtcaga tattcagaca tcaaaactta acgtgagctc agtggagtta     4980
cagctgcggt tttgatgctg ttattatttc tgaaactaga aatgatgttg tcttcatctg      5040
ctcatcaaac acttcatgca gagtttaagg ctagtgagaa atgcatacat ttattgatac      5100 tttttaaag tcaactttt atcagatttt tttttcattt ggaaatatat tgttttctag       5160 cgggccccccc ctcgaggtcg atcgagatct agcctgactg cggatccgca ggtcactgtg     5220
acctagatcc gcaggtcact gtgacctaca tctgatatca tcgtcgacgg tatcgataag     5280
cttcgaccga tccggccccg cccagcgtct tgtcattggc gaattcgaac acgcagatgc     5340
agtcggggcg cgcggtccg aggtccactt cgcatattaa ggtgacgcgt gtggcctcga      5400
acaccgagcg accctgcagc gacccgctta acagcgtcaa cagcgtgccg cagatctcga     5460
gagatctcga ggcatgcaag cttggcattc cggtactgtt ggtaaaatgg aagacgccaa     5520
aaacataaag aaaggcccgg cgccattcta tcctctagag gatggaaccg ctggagagca     5580
actgcataag gctatgaaga gatacgcct ggttcctgga acaattgctt ttacagatgc      5640
acatatcgag gtgaacatca cgtacgcgga atacttcgaa atgtccgttc ggttggcaga    5700
agctatgaaa cgatatgggc tgaatacaaa tcacagaatc gtcgtatgca gtgaaaactc    5760
tcttcaattc tttatgccgg tgttgggcgc gttatttatc ggagttgcag ttgcgcccgc    5820
gaacgacatt tataatgaac gtgaattgct caacagtatg aacatttcgc agcctaccgt    5880
agtgtttgtt tccaaaaagg ggttgcaaaa aattttgaac gtgcaaaaaa aattaccaat    5940
aatccagaaa attattatca tggattctaa aacggattac cagggatttc agtcgatgta    6000
cacgttcgtc acatctcatc tacctcccgg ttttaatgaa tacgattttg taccagagtc    6060
ctttgatcgt gacaaaacaa ttgcactgat aatgaattcc tctggatcta ctgggttacc    6120
taagggtgtg gcccttccgc atagaactgc ctgcgtcaga ttctcgcatg ccagagatcc    6180 tattttggc aatcaaatca ttccggatac tgcgatttta agtgttgttc cattccatca     6240
cggttttgga atgtttacta cactcggata tttgatatgt ggatttcgag tcgtcttaat    6300
gtatagattt gaagaagagc tgtttttacg atcccttcag gattacaaaa ttcaaagtgc    6360
gttgctagta ccaaccctat tttcattctt cgccaaaagc actctgattg acaaatacga    6420
tttatctaat ttacacgaaa ttgcttctgg gggcgcacct ctttcgaaag aagtcgggga    6480
agcggttgca aaacgcttcc atcttccagg gatacgacaa ggatatgggc tcactgagac    6540
tacatcagct attctgatta cacccgaggg ggatgataaa ccgggcgcgg tcggtaaagt    6600
tgttccattt tttgaagcga aggttgtgga tctggatacc gggaaaacgc tgggcgttaa    6660
tcagagaggc gaattatgtg tcagaggacc tatgattatg tccggttatg taaacaatcc    6720
ggaagcgacc aacgccttga ttgacaagga tggatggcta cattctggag acatagctta    6780
ctgggacgaa gacgaacact tcttcatagt tgaccgcttg aagtctttaa ttaaatacaa    6840
aggatatcag gtggcccccg ctgaattgga atcgatattg ttacaacacc ccaacatctt    6900
cgacgcgggc gtggcaggtc ttcccgacga tgacgccggt gaacttcccg ccgccgttgt    6960
tgttttggag cacggaaaga cgatgacgga aaaagagatc gtggattacg tggccagtca    7020
agtaacaacc gcgaaaaagt tgcgcggagg agttgtgttt gtggacgaag taccgaaagg    7080
```

```
tcttaccgga aaactcgacg caagaaaaat cagagagatc ctcataaagg ccaagaaggg    7140
cggaaagtcc aaattgtaaa atgtaactgt attcagcgat gacgaaattc ttagctattg    7200
taatactgcg atgagtggca gggcggggcg taattttttt aaggcagtta ttggtgccct    7260
taaacgcctg gtgctacgcc tgaataagtg ataataagcg gatgaatggc agaaattcgc    7320
cggatctttg tgaaggaacc ttacttctgt ggtgtgacat aattggacaa actacctaca    7380
gagatttaaa gctctaaggt aaatataaaa tttttaagtg tataatgtgt taaactactg    7440
attctaattg tttgtgtatt ttagattcca acctatggaa ctgatgaatg ggagcagtgg    7500
tggaatgcct ttaatgagga aaacctgttt tgctcagaag aaatgccatc tagtgatgat    7560
gaggctactg ctgactctca acattctact cctccaaaaa agaagagaaa ggtagaagac    7620
cccaaggact tccttcaga attgctaagt tttttgagtc atgctgtgtt tagtaataga    7680
actcttgctt gctttgctat ttacaccaca aaggaaaaag ctgcactgct atacaagaaa    7740
attatggaaa atattctgt aacctttata agtaggcata acagttataa tcataacata    7800
ctgttttttc ttactccaca caggcataga gtgtctgcta ttaataacta tgctcaaaaa    7860
ttgtgtacct ttagcttttt aatttgtaaa ggggttaata aggaatattt gatgtatagt    7920
gccttgacta gagatcataa tcagccatac cacatttgta gaggttttac ttgctttaaa    7980
aaacctccca cacctccccc tgaacctgaa acataaaatg aatgcaattg ttgttgttaa    8040
cttgtttatt gcagcttata atggttacaa ataaagcaat agcatcacaa atttcacaaa    8100
taaagcattt ttttcactgc attctagttg tggtttgtcc aaactcatca atgtatctta    8160
tcatgtctgg atccgtcgag ggggatccac tagttctaga gcggccgcca ccgggatcca    8220
taatataact gtaccaggtt ttggtttatt acatgtgact gacggcttcc tatgcgtgct    8280
cagaaaacgg cagttgggca ctgcactgcc cggtgatggt gccacggtgg ctcctgccgc    8340
cttctttgat attcactctg ttgtatttca tctcttgttg ccgatgaaag gatataacag    8400
tctctgagga aatacttggt atttcttctg atcagcgttt ttataagtaa tgttgaatat    8460
tggataaggc tgtgtgtcct ttgtcttggg agacaaagcc cacagcaggt ggtggttggg    8520
tggtggcagc tcagtgacag gagaggtttt tttgcctgtt tttttgttg tttttttttt    8580 ttaagtaagg tgttctttt tcttagtaaa atttctactg gactgtatgt tttgacaggt    8640
cagaaacatt tcttcaaaag aagaaccttt tggaaactgt acagcccttt tctttcattc    8700 ccttttgct ttctgtgcca atgcctttgg ttctgattgc attatggaaa acgttgatcg    8760
gaacttgagg tttttattta tagtgtggct tgaaagcttg gatagctgtt gttacatgag    8820
ataccttatt aagtttaggc cagcttgatg ctttattttt tttcctttga agtagtgagc    8880
gttctctggt ttttttcctt tgaaactggc gaggcttaga tttttctaat gggatttttt    8940
acctgatgat ctagttgcat acccaaatgc ttgtaaatgt tttcctagtt aacatgttga    9000
taacttcgga tttacatgtt gtatatactt gtcatctgtg tttctagtaa aaatatatgg    9060
catttataga aatacgtaat tcctgatttc cttttttttt tatctctatg ctctgtgtgt    9120
acaggtcaaa cagacttcac tcctattttt atttatagaa ttttatatgc agtctgtcgt    9180
tggttcttgt gttgtaagga tacagcctta aatttcctag agcgatgctc agtaaggcgg    9240
gttgtcacat gggttcaaat gtaaaacggg cacgtttgct gctgccttcc cagatccagg    9300
acactaaact gcttctgcaa ctgaggtata aatcgcttca gatcccagga agtgtagatc    9360
cacgtgcata ttcttaaaga agaatgaata ctttctaaaa tatgttgcat aggaagcaag    9420
ctgcatggat ttatttggga cttaaattat tttggtaacg gagtgcatag gttttaaaca    9480
```

```
cagttgcgag catgctaacg agtcacagca tttatgcaga agtgatgcct gttgcagctg    9540
tttacggcac tgccttgcag tgagcattgc agatagggggt ggggtgcttt gtgtcgtgtt    9600
gggacacgct gccacacagc cacctcccga acatatctca cctgctgggt actttttcaaa   9660 ccatcttagc agtagtagat gagttactat gaaacagaga agttcctcag ttggatattc    9720
tcatgggatg tctttttttcc catgttgggc aaagtatgat aaagcatctc tatttgtaaa   9780
ttatgcactt gttagttcct gaatcctttc tatagcacca cttattgcag caggtgtagg    9840
ctctggtgtg gcctgtgtct gtgcttcaat cttttaagct tctttggaaa tacactgact    9900
tgattgaagt ctcttgaaga tagtaaacag tacttacctt tgatcccaat gaaatcgagc    9960
atttcagttg taaaagaatt ccgcctattc ataccatgta atgtaatttt acaccccccag  10020 tgctgacact ttggaatata ttcaagtaat agacttggc ctcaccctct tgtgtactgt    10080
attttgtaat agaaatatt ttaaactgtg catatgatta ttacattatg aaagagacat    10140
tctgctgatc ttcaaatgta agaaaatgag gagtgcgtgt gcttttataa atacaagtga   10200
ttgcaaatta gtgcaggtgt ccttaaaaaa aaaaaaaaa agtaatataa aaaggaccag    10260 gtgtttaca agtgaaatac attcctattt ggtaaacagt tacatttta tgaagattac    10320 cagcgctgct gactttctaa acataaggct gtattgtctt cctgtaccat tgcatttcct    10380
cattcccaat ttgcacaagg atgtctgggt aaactattca agaaatggct ttgaaataca   10440
gcatgggagc ttgtctgagt tggaatgcag agttgcactg caaaatgtca ggaaatggat    10500
gtctctcaga atgcccaact ccaacaaagg attttatatg tgtatatagt aagcagtttc   10560
ctgattccag caggccaaga gtctgctgaa tgttgcgttg ccggagacct gtatttctca    10620
acaaggtaag atggtatcct agcaactgcg gattttaata cattttcagc agaagtactt    10680
agttaatctc tacctttagg gatcgtttca tcatttttag atgttatact tgaaatactg   10740
cataactttt agctttcatg ggttccttt tttcagcctt taggagactg ttaagcaatt    10800
tgctgtccaa cttttgtgtt ggtcttaaac tgcaatagta gtttaccttg tattgaagaa   10860
ataaagacca ttttttatatt aaaaaatact tttgtctgtc ttcattttga cttgtctgat   10920
atccttgcag tgctcattat gtcagttctg tcagatattc agacatcaaa acttaacgtg   10980
agctcagtgg agttacagct gcggttttga tgctgttatt attctgaaa ctagaaatga    11040 tgttgtcttc atctgctcat caaacacttc atgcagagtt taaggctagt gagaaatgca   11100
tacatttatt gatactttt taaagtcaac tttttatcag atttttttt catttggaaa    11160 tatattgttt tctacggtgg agctccaatt cgccctatag tgagtcgtat tacgcgcgct   11220
cactggccgt cgttttacaa cgtcgtgact gggaaaaccc tggcgttacc caacttaatc   11280
gccttgcagc acatccccct ttcgccagct ggcgtaatag cgaagaggcc cgcaccgatc   11340
gcccttccca acagttgcgc agcctgaatg gcgaatggaa attgtaagcg ttaatatttt   11400
gttaaaattc gcgttaaatt tttgttaaat cagctcattt tttaaccaat aggccgaaat   11460
cggcaaaatc ccttataaat caaaagaata daccgagata gggttgagtg ttgttccagt   11520
ttggaacaag agtccactat taaagaacgt ggactccaac gtcaaagggc gaaaaaccgt   11580
ctatcagggc gatggcccac tacgtgaacc atcaccctaa tcaagttttt tggggtcgag   11640
gtgccgtaaa gcactaaatc ggaacccctaa agggagcccc cgatttagag cttgacgggg   11700
aaagccggcg aacgtggcga gaaaggaagg gaagaaagcg aaaggagcgg gcgctagggc   11760
gctggcaagt gtagcggtca cgctgcgcgt aaccaccaca cccgccgcgc ttaatgcgcc   11820
gctacagggc gcgtcag                                                  11837
```

TRANSGENIC MOUSE FOR SCREENING AND FOR STUDIES OF THE PHARMACODYNAMICS AND PHARMACOKINETICS OF LIGANDS ACTING ON THE OESTROGEN RECEPTOR AND ITS INTRACELLULAR RECEPTORS, AND METHOD FOR THE PREPARATION THEREOF

Research carried out in the last ten years has shown that oestrogen deficiency is associated with an increased risk of the appearance of a large number of diseases of the nervous, immune, cardiovascular and bone systems. These studies thus suggest that the oestrogens, traditionally considered to be hormones responsible solely for the control of the reproductive functions, in fact have an important role in the maintenance of the homeostasis of many tissues in the mammal (for a review, see Nilsson and Gustafsson, 2000); pharmacological research is thus directed towards the obtaining of therapeutically active molecules which can be substituted for the hormone in order to exert their protective and beneficial activity solely in specific target organs.

Meanwhile, research at the molecular and cellular level has clarified the mechanism by which the hormone acts on the target cells (for a review, see Tsai and O'Malley, 1994). In particular, the hormone recognises and binds to intracellular proteins, called oestrogen receptors (so far, two types of receptor, designated by the first two letters of the Greek alphabet, are known). The hormone-receptor complex is then enabled for the recognition of specific sequences of DNA (called hormone response elements), for interaction with other protein factors (some of them ubiquitous and others tissue-specific) for the activation of the transcription of the target genes. This mechanism provides the molecular basis for the explanation of an observation made with synthetic ligands of the oestrogen receptors, namely that these can function as receptor agonists in some organs and antagonists in others.

At present, a considerable number of pharmaceutical multinationals are involved in the development of molecules for use in replacement therapies, which may be capable of acting as activators of oestrogen receptors in some organs and as antagonists in others. For example, in the case of the oestrogen receptor, molecules are currently being sought which activate this receptor in organs such as bone and brain, but not the uterus and mammary tissue where the trophic activity of the receptor could favour the onset of neoplasias.

The bottleneck in these studies comprises the identification of the molecules endowed with the desired agonistic/antagonistic activity. At present, the screening of such molecules is carried out in transformed cell lines suitably engineered to express an exogenous marker gene of hormonal activity.

The limits of this type of methodology are connected with the fact that this technique is performed on immortalised/neoplastic cells, which are thus modified with respect to the physiological target; further, it does not provide any information concerning the pharmacokinetics and the bioavailability of the compound with potential pharmacological activity. For these reasons, the ligands identified by screening on cells must in any case be subjected to tests on animals. Finally, not all the areas of the organism which are targets of these hormones are yet fully known. According to the present invention, it was decided to overcome these limitations by the generation of a mouse engineered so that it expresses the marker gene of hormonal activity in all its cells and tissues. Hence, the administration to such a mouse of any compound with oestrogenic activity would result in an accumulation of the gene product in those organs/cells where the compound acts as a receptor agonist. This mouse represents an ideal system for the screening of molecules acting on the oestrogen receptors in that:

1. It allows the simultaneous visualisation of all the organs/cells in which the compound under test exerts a pharmacological activity (including cells whose responsivity to the hormone is unknown).

2. It makes it possible to know the distribution of the compound (for example whether it penetrates the blood-brain barrier).

3. It makes it possible also to carry out pharmacokinetic studies to clarify the catabolism of the ligand in question, and its absorption times as well as its possible persistence and activity in all parts of the mouse, allowing the prediction of possible side-effects. Such methods can be carried out in vivo by non-invasive imaging methodologies.

Another use of the animal model according to the invention concerns the ecotoxicology field. One of the major environmental contamination problems is connected with the activity of the so-called xenooestrogens. It has been proved that many synthetic substances widely used in agriculture (e.g. atrazine) and other compounds present in industrial wastes (e.g. dioxin) display active interference with the endocrine system in mammals causing strong repercussions on the reproductive system right up to sterility; the increase in such substances in the environment is now recognised as one of the causes of increased sterility in man (Sharpe and Skakkebaek, 1993). It will thus also be possible to use the animal as a biosensor for specific environmental pollutant substances (e.g. pesticides).

Finally, it will be possible to use the animal as a source of cells for in vitro culturing. Primary or immortalised cultures from different tissues can be obtained by standard cell culturing protocols. Such cultures can be used in the screening of compounds with hormonal action.

The invention here described concerns the generation of a transgenic animal. As is well-known, the transgenics are animals into whose chromosome apparatus an exogenous gene has been inserted and are capable of transmitting it to their progeny. Two basic procedures exist for the generation of transgenic animals which were initially developed in the mouse: 1. the microinjection of the fragment of DNA into the genome at the single-cell stage, in the male pronucleus of a fertilised oocyte and its reimplantation into pseudogravid females (Constantini and Lacy, 1981; Gordon and Ruddle, 1981); 2. the transfection of the DNA into embryonic stem cells and the injection of these into the blastocysts (Robertson et al., 1986; Gossler et al., 1986). Various other animal species have been engineered in this way: for example Hammer and coworkers (1985) have described the application of trangenesis in rabbits, in sheep and in pigs. The mouse is still an animal much utilised in transgenesis and is also the first transgenic animal to have been patented (EP 0169672B1).

The present invention relates to a method for the production of a non-human transgenic mammalian animal by means of which it is possible to monitor in vivo and in all the tissues the activation state of an intra-cellular receptor, characterized in that a reporter gene whose transcription is inducible by synthetic or natural molecules which modulate the activity of such a receptor is incorporated into the genome of the animal.

Therefore, in the following the said reporter gene will also be referred to as reporter transgene.

More specifically, the present invention provides a method for the production of a transgenic mammalian animal utilisable as an experimental model for simultaneously monitoring in vivo the pharmacological activity, the tissue-specificity, the pharmacokinetics and the pharmaco-dynamics dynamics of molecules with potential activity on intracellular receptors.

Generation of the Animal Model

The transgenic model which is the object of the present invention can be obtained by the integration into the somatic and germinal line of a gene called a reporter, provided with control regions that make its expression inducible by such hormones. The gene in question is not present in the genome of the mammal and codes for an enzyme easily quantifiable by an enzyme test. Any reporter gene is utilisable for the purposes of the present invention. A list of reporter genes currently available are [sic] indicated, together with some of their characteristics, in Table I given later. These are luciferase, green fluorescent protein (GFP), beta-galactosidase, beta-lactamase and chloramphenicol acetyltransferase (CAT).

Also mentioned are dopamine 2 receptor (D2R) and thymidine kinase (TK).

The possibility of hormone-dependently inducing the transcription of a reporter gene is a function of the presence of specific sequences to which the ligand-receptor complex binds. In particular according to the invention a series of constructs consisting of palindromic sequences responsive to oestrogens (ERE) shown in FIG. 2 of the attached drawings, and described later, was generated. They are:

ERE4X

ERE2X-33 bp linker-ERE2X, and

ERE2X, wherein

ERE2X or 4X=oestrogen-responsive element multimerised 2- or 4-fold, respectively and 33 bp linker=non-responsive DNA linking sequence between the ERE.

Of these, the construct utilised for the generation of the oestrogen-responsive transgene according to the invention preferably has the following structure:

ERE2X.

Such sequences were placed upstream of a promoter which does not display tissue-specificity, such as the constitutive promoter of the gene for viral thymidine kinase, TKprom. The promoter of the final construct is thus constituted as follows:

ERE2X-TKprom-Reporter.

A constitutive promoter according to the invention can also be a minimal promoter consisting of TATA box and transcription initiator sequence.

In the tissues of the model animal presented, the administration of agonists causes an increase in the activity of the protein encoded by the reporter; this increase depends specifically on the presence of intracellular receptors activated by the ligand in the target cell and is proportional to the degree of hormonal stimulation. In other words, the expression of the transgene constitutes a signal of the existence of some activity of the specific hormone in some specific body area of the transgenic mouse. The model also allows the study of molecules with antagonistic activity towards oestrogen receptors. In this case, the evaluation of the antagonistic activity of the molecule in question will be effected in animals simultaneously treated with oestrogens to evaluate the blocking of the hormonal activity by the presumed antagonist.

The stable introduction of an ERE-TKprom-Reporter construct into the genome of fertilised oocytes or of embryonic stem cells makes it possible to obtain a first series of individuals (called founders). From these founders are obtained, via hereditary transmission, firstly the heterozygotic individuals and then the homozygotic individuals for the transgene which will be inherited in the Mendelian manner in case of insertion into a unique site. However, the expression of the transgene inserted in this manner into the animal is subject to the so-called positional effect, namely the influence of the chromatin surrounding the site of insertion into the genome. As a result, the transgene will be expressed or not expressed, in an incorrect manner and often with undesired tissue preferences. This phenomenon, called PVE (Position Variegation Effect), is typical of eukaryotic cells and has been amply characterised and studied; it was the principal cause of the failure of preceding attempts to generate the animal model which is the object of this patent. To circumvent this problem, according to the present invention suitable sequences called insulators were used, which, placed at the flanks of the transgene, have the ability to isolate it from the effect of the heterochromatin and from surrounding enhancer sequences (for a review, see Fang-Lin and Elgin, 1999). Some of these sequences are shown in Table II.

The final constructs, or plasmids, utilised for the transgenesis of the mouse which is the object of the present invention were constituted as follows (FIG. 3):

pMAR=MAR-ERE2X-TKpr-Luciferase-MAR pHS4=HS4-ERE2X-TKpr-Luciferase-HS4.

The screening system developed according to the present invention can be extended to any ligand acting on intracellular receptors. In this case the DNA sequence responsive to the hormone is selected among those known and available as described in Table III below, such as PRE, GRE, RARE, TRE, VD3RE and PPRE.

The Figures cited above are described below:

PREPARATION OF THE CONSTRUCTS

Figure 1:
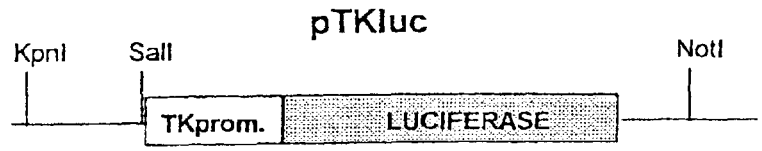
FIG. 1 is the schematic representation of the starting expression plasmid containing the luciferase reporter gene under the control of the constitutive promoter of viral thymidine kinase (TK).

The starting construct pTKluc described in FIG. 1 was obtained by subcloning the luciferase gene from pGL2basic (Promega) into the BamHI site of pBluescript (Stratagene); the −109 bp fragment of the TK promoter was isolated from the vector pBLCAT2 (Luckov and Schutz, 1987) and subcloned in the HindIII site of pBluescript. The construct obtained (pTKluc) was sequenced and the expression of luciferase was verified in MCF-7 human mammary carcinoma cells.

Figure 2:
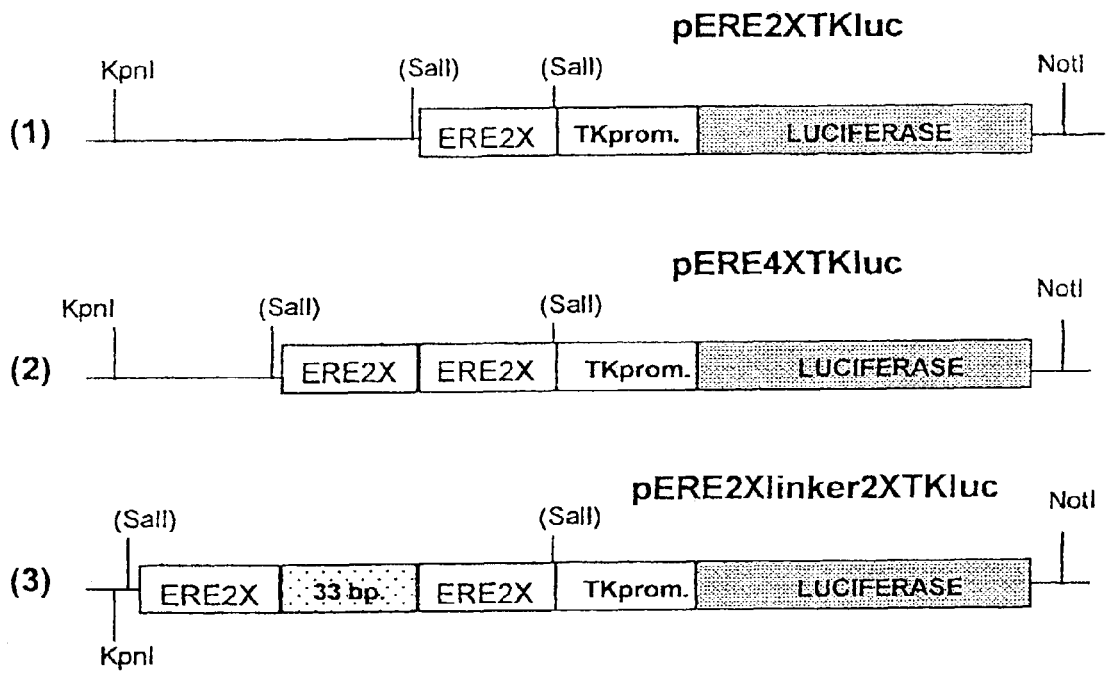
FIG. 2 is the schematic representation of the plasmids tested for inducibility by oestrogens, in which are present the ERE sequences, upstream of the TK promoter and with various arrangements: the ERE palindromes have been dimerised (1), or tetramerised with (3) or without (2) spacing sequences.

The oestrogen-responsive sequence (ERE), see Table III below, multimerised in the various arrangements described in FIG. 2, was subcloned in the SaiI site of pTKluc; the oestrogen-responsivitiy of the constructs thus obtained was examined in MCF-7 cells and in human neuroblastoma cells SK-N-BE. The highest responsivity to oestradiol was obtained from the construct pERE2X-TKluc (FIG. 2) which was chosen for generation of the final vectors utilised in the transgenesis.

Figure 3:
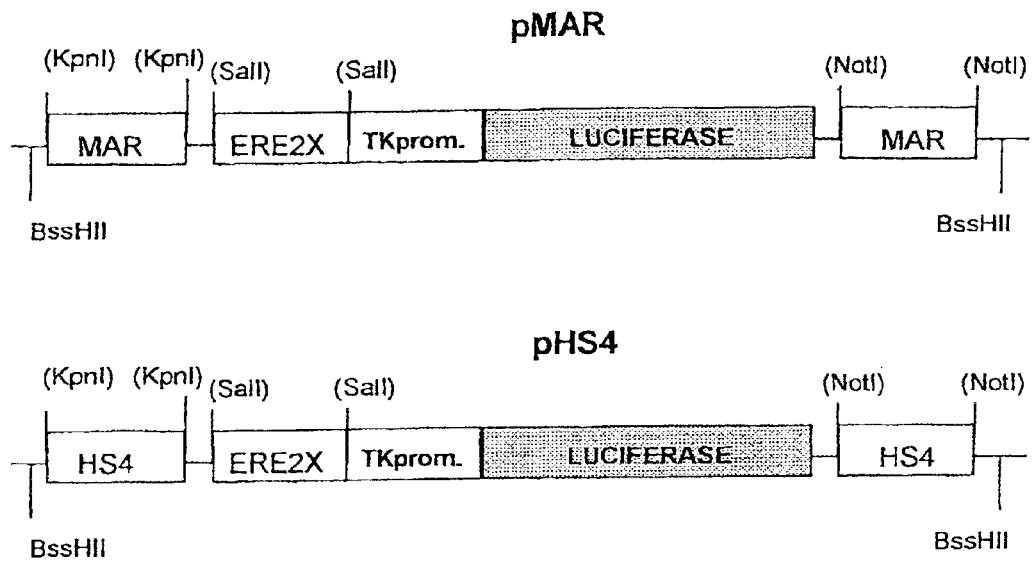
FIG. 3 is the schematic representation of the fusion of the insulator sequences MAR and HS4 with the plasmid ERE2X-TK-luciferase.

The insulators HS4 (Chung et al., 1993) and MAR (Stief et al., 1989) were subcloned into the flanking regions of pERE2XTKluc in the KpnI and NotI sites generating the vectors pHS4 and pMAR (FIG. 3).

Figure 4:
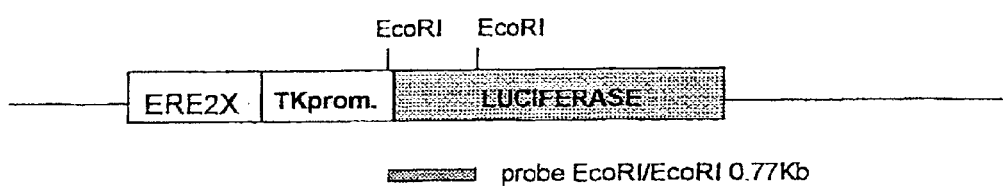
FIG. 4 is the schematic representation of the 0.77 Kb EcoRI/EcoRI probe used for the screening of the transgenic mice generated with the pMAR and pHS4 constructs.

The probe used in the screening of the transgenic animals (FIG. 4) was obtained by digestion of the plasmid pERE2XTKluc with the restriction enzyme EcoRI and the 0.77 Kb fragment was separated by electrophoresis on agarose gel and purified by electroelution (Maniatis et al., 1982).

Production of Transgenic Mice

The DNA fragments containing the transgenes were obtained from the plasmids pMAR and pHS4 by digesting them with the restriction enzyme BsshII and thus releasing the inserts of 8.95 Kb and 7.85 Kb respectively (FIG. 3); the transgenes were purified by electrophoresis on agarose gel and subsequent electroelution procedure (Maniatis et al., 1982). About 400 copies of the insert thus purified were injected into the male pronucleus of a fertilised egg deriving from individuals of the B6D2F1 strain of mouse. The mice were obtained from the Charles River Laboratories. The injected eggs were reimplanted into pseudo-gravid females. In this way, about 100 individuals were obtained. At the age of four weeks, the DNA from the biopsy of the tails of these individuals was extracted (Maniatis et al., 1982). About 10 µg of DNA for each sample were immobilised with a Slot Blot device (Schleicher and Schuell) on nylon filters (HybondN, Amersham). The filters obtained were subjected to hybridisation experiments with the 0.7 Kb EcoRI/EcoRI DNA probe described in FIG. 4, labelled with $^{32}$P using a kit based on the multiprimer principle, according to the producer's instructions (Megaprime DNA labelling system, Amersham). The hybridisation procedure was effected essentially as previously described (Maniatis et al., 1982); in particular, the hybridisation temperature used was 60° C. and the washings were performed in a solution containing 0.1×SSC/0.1% SDS (3 washings of 10 minutes at ambient temperature and 2 washings of 30 minutes at 60° C.).

The screening of the founders, effected as previously described, made it possible to identify 17 mice with the transgene integrated: 10 pMAR and 7 pHS4. Only 12 founders succeeded in generating fertile progeny positive for the presence of the transgene.

The number of copies integrated in the different lines is variable from one to thirty.

The founders were crossed with non-injected animals from the same original strain (B6D2F1) and the new-born at the age of four weeks were analysed for the presence of the transgene as described for the founders, by means of the Slot Blot technique.

Through successive recrossing of each of the 12 fertile lines, heterozygotic individuals and in the end also homozygotic lines were obtained.

Analysis of the Transgenic Mice

Figure 5:
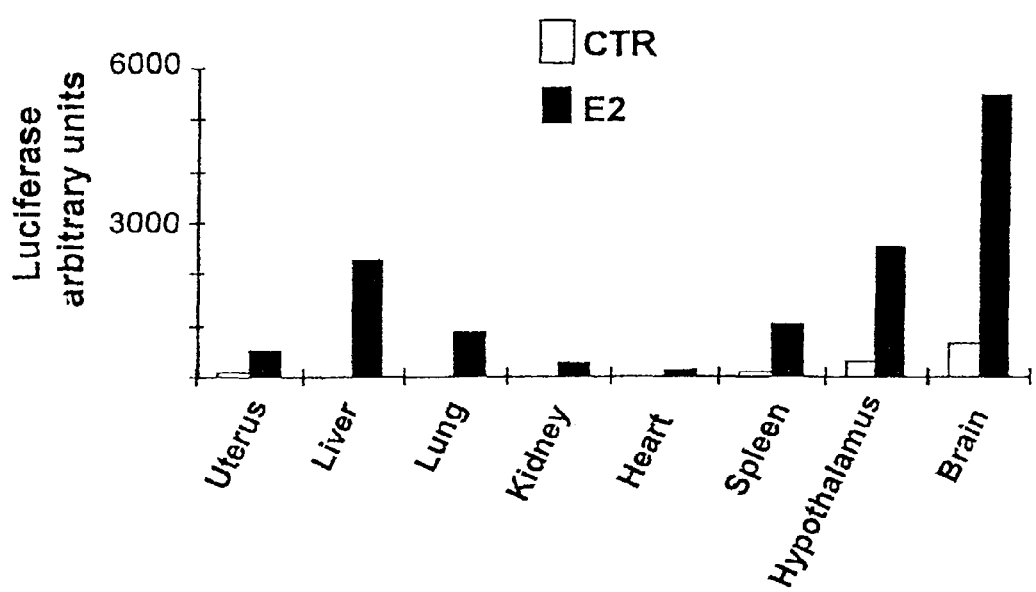
FIG. 5 is a chart showing luciferase activity in line 2 of transgenic mice.
Figure 6:
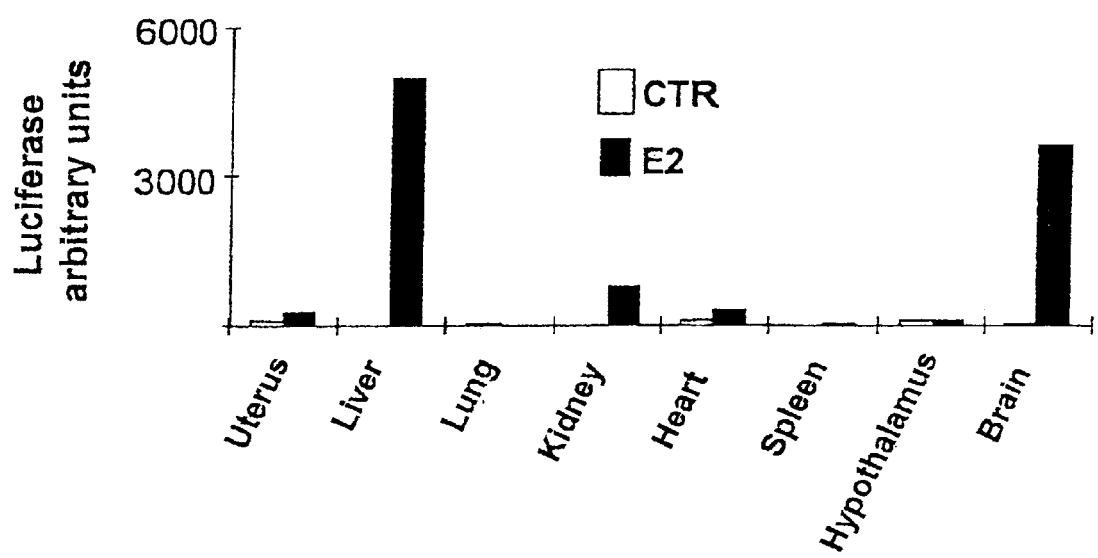
FIG. 6 is a chart showing luciferase activity in line 61 of transgenic mice.
Figure 7:
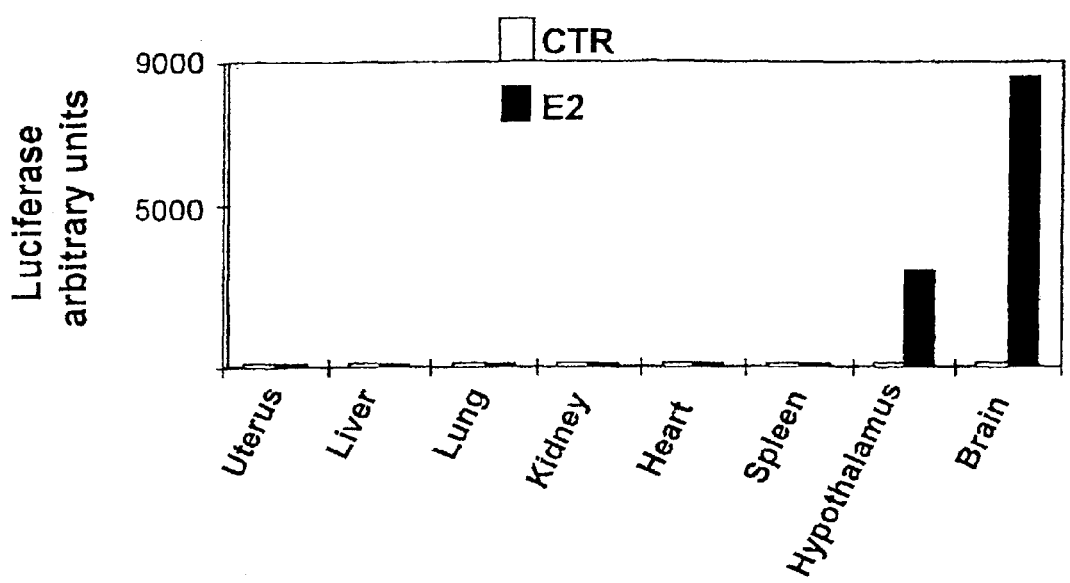
FIG. 7 is a chart showing luciferase activity in line 59 of transgenic mice.

To verify the expression of the transgene in the different tissues and its inducibility by oestrogens, 4 independent experiments were carried out on 8 female individuals of each line (4 heterozygotic and 4 homozygotic). For each experiment, two female individuals were ovariectomised. With the aim of reducing the oestrogens present in the bloodstream of the ovariectomised animals below the detection limit, there was a wait of two weeks before the induction experiment was carried out; the individuals were then subjected to subcutaneous (s.c.) injection of mineral oil with or without 50 µg/kg of dissolved 17-β oestradiol; 16 hours after the treatment, the individuals were sacrificed and the following tissues were dissected out of them: uterus, liver, spleen, lung, heart, kidney, hypothalamus and brain. The protein extracts were obtained by disintegration of the tissue with a homogenizer in the presence of a phosphate lysis buffer consisting of: 0.1 M $KH_2PO_4$, 0.1 M $K_2HPO_4$, 1 mM DTT, 4 mM EGTA and 4 mM EDTA at pH 7.8. The suspension was frozen and thawed three times, and centrifuged for 30 minutes at 13,000 g; the supernatant was collected and equal quantities of protein, measured by the colorimetric method of Bradford, were subjected to enzymatic testing to reveal the activity of the enzyme luciferase. The method for detection of the activity of the reporter was carried out with a kit by the procedure recommended by the producer (Sigma), mixing ca. 20 µg of protein extract with the luciferin substrate in the presence of 0.5 mM ATP and 30 mM DTT and measuring the fluorescence emitted using a luminometer (Lumat BL 9500, Berthold). With reference to FIGS. 5 to 7 of the attached drawings, individuals were subcutaneously injected (s.c.) with 50 µg/Kg 17β-estradiol (E2) or with vehicle (vegetable oil) and sacrificed at 24 hours. Luciferase enzymatic activity was evaluated and plotted in the graph. The arbitrary units are obtained considering the luciferase activity in the uterus of control individuals=100.

FIG. 5 shows the expression of luciferase in line 2 of the transgenic mice treated with 50 µg/kg of 17-β oestradiol (s.c.) for 24 hours, FIG. 6 shows the expression of luciferase in line 61 of the transgenic mice treated with 50 µg/kg of 17-β oestradiol (s.c.) for 24 hours, and FIG. 7 shows the expression of luciferase in line 59 of the transgenic mice treated with 50 µg/kg of 17-β oestradiol (s.c.) for 24 hours.

Of the 10 lines analysed, one (line 2, transgene pMAR) displayed ubiquitous and inducible expression of the transgene (FIG. 5); one was found to be inducible predominantly in the brain and in the liver (line 61, transgene pHS4) (FIG. 6), and one is inducible in the brain and in the hypothalamus (line 59, transgene PMAR) (FIG. 7).

Figure 8:
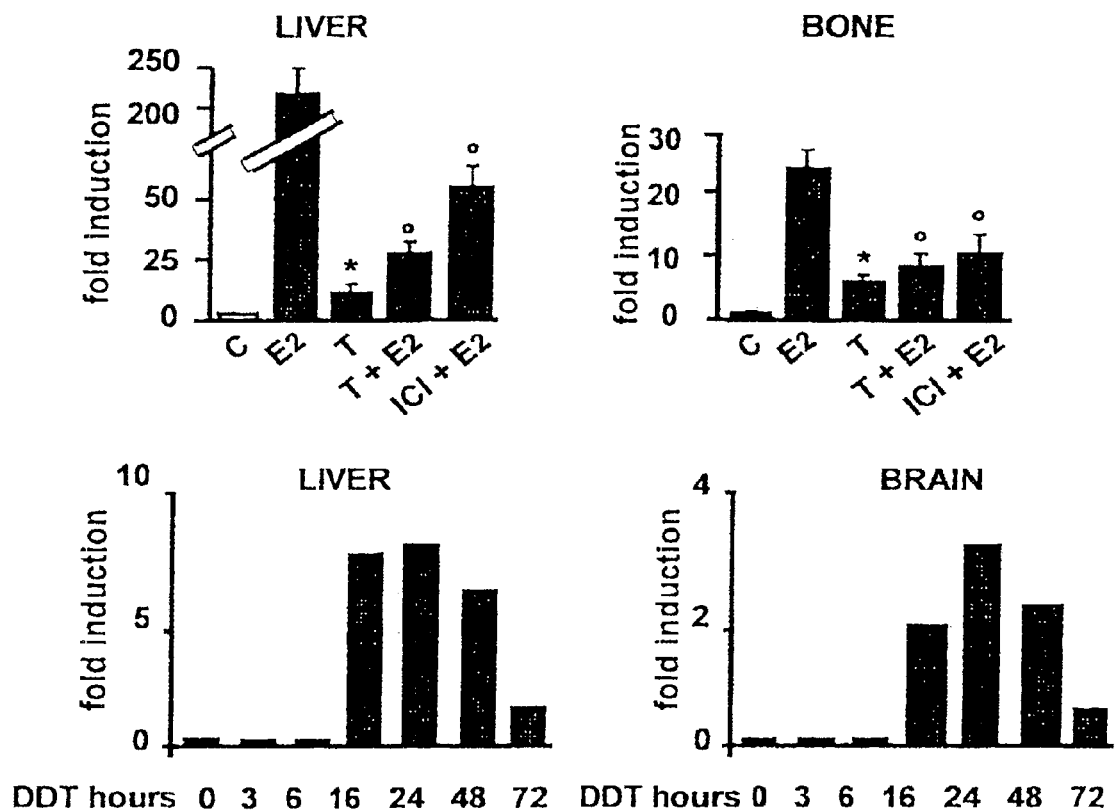
FIG. 8 shows pharmacological modulation of luciferase activity in vivo in bone and liver protein extracts of two months old male mice.

Test for the Agonistic and Antagonistic Action of a Compound and for the Activity of Xenooestrogens The animal of this invention can be utilised to test the ability of a compound to behave as an agonist or as an antagonist in the various tissues. By subcutaneous injection of the substance in the presence or in the absence of 17-β oestradiol it is in fact possible to compare the distribution and the intensity of expression of the luciferase gene in the various tissues and to compare it with the control or with the injection of 17-β oestradiol alone. The effect of in vivo administration of two known ER antagonists was investigated in line 2 of transgenic mice. FIG. 8 (upper panel) shows blockade of 17-β oestradiol (E2) activation by 4-hydroxytamoxifen (T) and ICI 182,780 (ICI) and partial agonist activity of tamoxifen (T) in liver and brain. Bars represent the average±s.e.m of 5-7 mice. *(P< 0.01 as compared to the control), °(P<0.01 as compared to the E2-treated); P were calculated with ANOVA followed by Scheffé test. Ligands were administered at the following doses: E2 50 µg/Kg, 4-hydroxytamoxifen and ICI 182,780 250 µg/Kg. Luciferase is expressed as fold induction obtained as the ratio between luciferase activity in ligands treated/control mice.

With reference to the upper panel of FIG. 8, s.c. administration of 250 μg/kg of 4-hydroxy-tamoxifen for 6 hours increased the level of luciferase in the liver 12-fold and 7-fold respectively, confirming in vivo the partial agonist activity of 4-hydroxytamoxifen in these tissues. The injection of 250 μg/kg of tamoxifen or ICI 182,780 one hour before the administration of 50 μg/kg of E2 inhibits the E2-dependent activation of luciferase expression as expected from the antagonistic effect of the compounds with respect to E2.

The animal of this invention can be utilised to verify the interference of environmental contaminants (pesticides, fertilisers, etc.) with the endocrine system, by administration of these by the transdermal or subcutaneous route or via the diet. The effects of a paradigmatic xenooestrogen, the organochlorine DDT, were investigated in our model. FIG. 8 (lower panel) shows the luciferase activity evaluated in the liver and brain (two known target organs for DDT toxicity) of individuals injected s.c. with 5000 μg/ml DDT and sacrificed at 3, 6, 16, 24, 48 or 72 hours. As shown, at 24 hours, maximal induction of luciferase activity was detected in both liver and brain compared to a control animal injected with vegetable oil (vehicle); this induction persisted until 72 hours.

Pharmacokinetics and Pharmacodynamics of E2 in the Transgenic Animals

Figure 9:
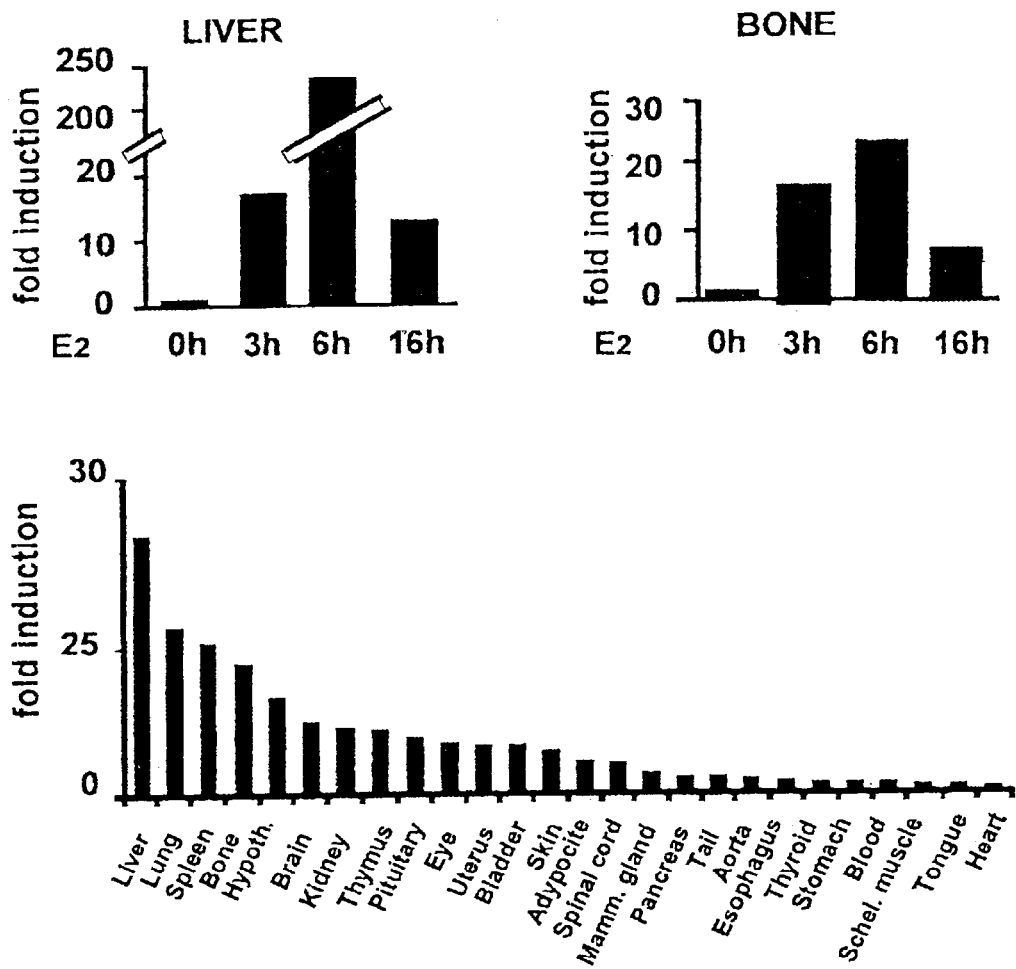
FIG. 9 shows time course of luciferase activity in liver and bone of transgenic mice treated with 17β-estradiol (E2) and tissue distribution of the E2-dependent luciferase induction within several tissues.

The pharmacokinetics of any compound acting via intracellular receptors can be studied in the animal of the invention, if the reporter used codes for a protein with a fast turnover in mammalian cells (e.g. luciferase, which has a 3 hour half-life in mammalian cells). This feature is required in order to follow the variation in receptor activation with time. FIG. 9 (upper panel) shows a pharmacokinetic study of E2 in the transgenic animal generated; individuals were injected s.c. with 50 μg/kg of E2 and sacrificed after 3, 6 or 16 hours. The maximal luciferase accumulation was observed at 6 hours in bone and liver, which correlates with the expected peak of oestrogen receptor transcriptional activity. Luciferase activity is expressed as fold induction as defined in FIG. 8. Bars are representative of the average values of at least 5 individuals.

The pharmacodynamics of any compound acting via intracellular receptors can also be correctly predicted by the transgenic model of the invention. As an illustrative example, ovariectomised luciferase activity was measured in 26 different tissues from 2-month old female mice which had been ovariectomised 2 weeks prior to the experiment. Mice were treated for 16 hours with either vehicle or E2 subcutaneously (s.c.). FIG. 9 (lower panel) shows that hormonal treatment induced an increase in the enzyme content compared to controls in oestrogen target organs. This distribution is very consistent with the reported tissue distribution of oestrogen receptors.

Tissue Cultures

Figure 10:
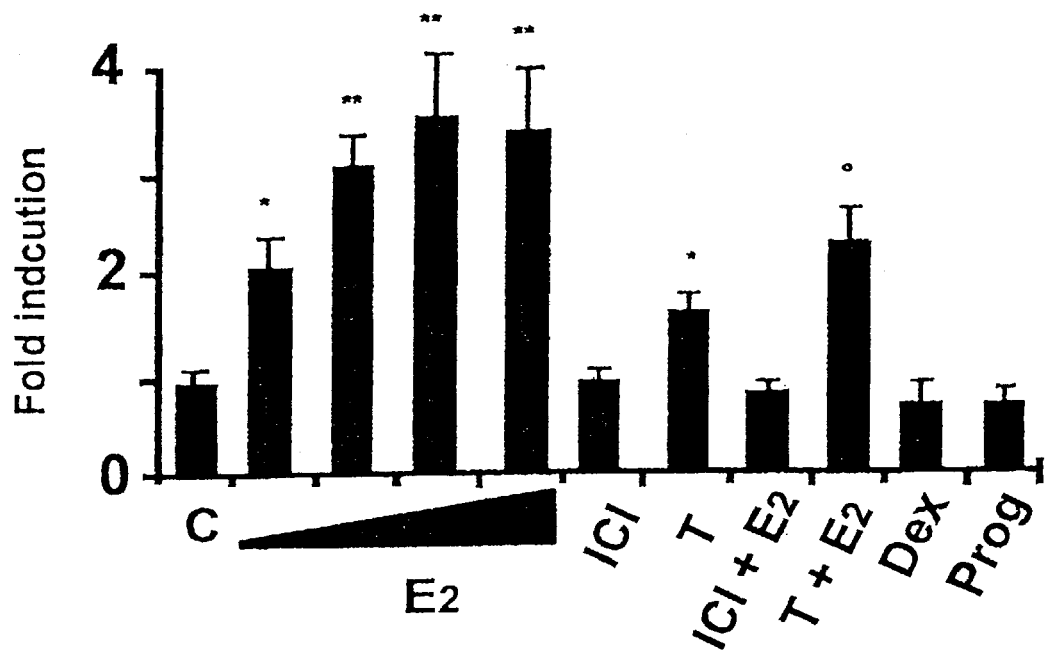
FIG. 10 is a chart showing expression of luciferase in primary bone marrow cells from transgenic mice.

The tissues of the animal which is the object of this invention can further be utilised as sources of cells for in vitro culture by means of standard culturing techniques. These techniques make it possible to obtain primary cultures which can be utilised directly as nontransformed lines for the screening of substances with oestrogenic activity, or can be transformed in order to obtain lines whose cells continue to proliferate. As an example of such an application, bone marrow cells from the transgenic mouse generated were obtained and used in a pharmacological study; the results are summarised in FIG. 10. Two millions of bone marrow cells were suspended in phenol red-free RPMI 1640 with 10% stripped serum. Cells were treated with vehicle (C), with increasing concentrations of E2 (0.001; 0.01; 0.1; 1 and 10 nM), with 100 nM ICI 182,780 (ICI) with 4-hydroxytamoxifen (T) either alone or with 1 nM E2; progesterone (Prog) and dexametasone (Dex) were used at 10 nM final concentration. Bars represent the average±s.e.m. of 5 individual experiments each done in triplicate. *($p<0.01$ as compared to the control), **($p<0.005$ as compared to the control), °($p<0.05$ as compared to the T-treated); $P$ were calculated with ANOVA followed by Scheffé test. The cells were treated for 16 hours with increasing concentrations of E2 (0.01-10 nM) or with 100 nM of two ER antagonists: 4-hydroxytamoxifen (T) and ICI 182,780 (ICI) alone or in the presence of 1 nM E2. E2 induced a dose-dependent increase in luciferase accumulation blocked by the presence of ICI 182,780. ICI 182,780 by itself did not sort [sic] any effect. Conversely, 4-hydroxytamoxifen induced a significant increase in luciferase levels even though lower than E2 at the same concentration. On co-administration with E2, 4-hydroxytamoxifen induced higher luciferase accumulation, yet the level reached was still lower than with E2 alone. This is compatible with the partial agonist activity of 4-hydroxytamoxifen and with the fact that it is present in the solution at a concentration 100 times higher than that of E2. As a control, we also tested progesterone and dexamethasone (10 nM). Both ligands did not have any effect on the ER reporter. Taken together, these date confirm that primary cells can be explanted from the engineered mice; the transgene is controlled by ligands of ER with modalities recapitulating those reported for the natural target genes.

Deposits

The plasmids utilised for the transgenesis, described in FIG. 3, have been deposited at the ECACC (European Collection of Cell Cultures) Institute, Salisbury, Wiltshire SP4 OJG, UK, the recognized IDA under the Budapest Treaty on the International Recognition of the Deposit of Microorganisms for the Purposes of Patent Procedure, on Apr. 11, 2000, and have been given the following access numbers: pMAR00041120 and pHS400041121.

The sequences of the plasmids have been deposited at the EMBL (European Molecular Biology Laboratory) Institute, Heidelberg, Germany, and have been given the following access numbers: pHS4=AJ277959 (SEQ ID NO: 9) and pMAR=A277960 (SEQ ID NO: 10).

Finally, the list of literature references cited is given.

Costantini F and Lacy E., (1981) Nature, 294: 92-94.
Chalfie M., Tu Y., Euskirchen G., Ward W. W. and Prasher D. C. (1994) Science, 263: 802-805.
Chung J. H., Whiteley M and Felsenfeld G. (1993) Cell, 74: 505-514.
De The H., Vivanco Ruiz M. D. M., Tiollais P., Stunnenberg H. and Dejean A. (1990) Nature, 343, 177-180.
de Wet J. R. et al. (1987) Mol. Cell. Biology, 7: 725.
Durand B., Saunders M., Leroy P., Leid M. and Chambon P. (1992) Cell, 71: 73-86.
Fang-Lin S. and Elgin S. C. R. (1999) Cell, 99: 459-462.
Fu Y., Wang Y and Evans S. M. (1998) Nature Biotechnology, 16: 253-257.
Gordon J. W. and Ruddle F. H. (1981) Science, 214: 1244-1246.
Gorman C. M., Moffat L. F. and Howard B. H. (1982) Mol. Cell. Biol., 2: 1044.
Gossler A. T., Doetschman R., Korn E. and Kemler R. (1986) Proc. Natl. Acad. Sci. USA, 83: 9065-9069.
Klein-Hitpass L., Schorpp M., Wagner U., Ryffel G. U., Kliewer S. A. and Umesono K. (1986) Cell, 46: 1053-61.
Noonan D. J., Heyman R. A. and Evans R. M. (1992) Nature, 358: 771-774.
Luckow B. and Schutz G. (1987) Nucleic Acids Res., 15: 5490.

Maniatis T., Fritsch E. F. and Sambrook J. (1982) Cold Spring Harbor Laboratory Press. Cold Spring Harbor, N.Y.

Miller J. H. (1972) Cold Spring Harbor Laboratory Press. Cold Spring Harbor, N.Y.

Nilsson S and Gustafsson J-A (2000) in press.

Noda M., Vogel R., Craig A. M., Prahl J., DeLuca H. F. and Denhardt D. T. (1990) Proc. Natl. Acad. Sci. USA, 87: 9995-9999.

Robertson E. A., Bradley M. and Evans M. (1986) Nature, 323: 445-448.

Sap J., de Magistris L., Scmitt J., Stunnenberg H. and Vennenstrom B. (1990) EMBO J., 9: 887-896.

Sharpe R. M. and Skakkebaek N. E. (1993) Lancet, 341: 1392-1395.

Stief A., Winter D., Stratling W. H. and Stippel A. E. (1989) Nature, 341: 343-345.

Stunnenberg H. G. (1993) Bioessays, 15: 309-15.

Tsai M-J. and O'Malley B. W. (1994) Ann. Rev. Biochem., 63: 451-486.

von der Ahe D., Janich S., Scheidereit C., Renkawitz R., Schutz G. and Beato M. (1985) Nature, 313: 706-709.

Zlokarnik G., Negulescu P. A., Knapp T. E., Mere L., Burres N., Feng L., Whitney M., Roemer K. and Tsien R. Y. (1998) Science, 279: 84-88.

TABLE I

| Reporter | Enzymatic test | Detection in vital cells | References |
| --- | --- | --- | --- |
| Luciferase | yes | yes | de Wet 1987 |
| Green fluorescent protein | no | yes | Chalfie et al., 1994 |
| beta galactosidase | yes | no | Miller 1982 |
| beta lactamase | yes | yes | Zlokarnik et al., 1998 |
| chloramphenicol acetyl-transferase | yes | no | Gorman et al., 1982 |

TABLE II

| Insulator | Gene of origin | References |
| --- | --- | --- |
| HS4 | chicken beta-globin | Chung et al., 1993 |
| MAR | chicken lysozyme | Stief et al., 1989 |
| ITR | adeno-associated virus | Fu et al., 1998 |

TABLE III

| Responsive sequence | Sequence recognised | Gene regulated by the responsive element cited | Receptor that binds the responsive sequence | References |
| --- | --- | --- | --- | --- |
| ERE | ggtca(n)$_3$tgacc (SEQ ID NO: 1) | vitellogenin | oestrogen receptor | Klein-Hitpass L, et al., 1986 |
| GRE/PRE | agaaca(n)$_3$tgttct (SEQ ID NO: 2) | MMTV | glucocorticoid and progesterone receptors | von der Ahe D. et al., 1985 |
| RARE | ggttca(n)$_5$agttca (SEQ ID NO: 3) | RAR-β2 | retinoic acid receptor | De The et al, 1990 |
| | agttca(n)$_2$aggtca (SEQ ID NO: 4) | CRABPII | | Durand et al., 1992 |
| | agttcanaggtca (SEQ ID NO: 5) | CRABPII | | |
| TRE | gggtca(n)$_4$aggtcc (SEQ ID NO: 6) | growth hormone | thyroid hormone receptor | Sap et al., 1990 |
| VD$_3$RE | gttca(n)$_3$ggttca (SEQ ID NO: 7) | osteopontin | vitamin D receptor | Noda et al, 1990 |
| PPRE | aggtcanaggtca (SEQ ID NO: 8) | acyl CoA oxidase | peroxysome proliferation factor receptor | Kliewer et al, 1992 |

The invention claimed is:

1. A plasmid defined by the ECACC access number pMAR00041120.

2. A plasmid defined by the ECACC access number pHS400041121.

3. A transgenic mouse whose genome comprises a transgene comprising a reporter transgene operatively ligated to a constitutive non tissue-specific promoter containing one or more intracellular receptor/transcription factor responsive elements; said promoter-reporter construct being MAR(matrix attachment regions)-ERE(oestrogen receptor responsive element)2X-TKpr(thymidine kinase promoter)-Luciferase-MAR or HS4(beta-globin hypersensitive site 4)-ERE2X-TKpr-Luciferase-HS4, wherein, when 17-beta estradiol is administered to the transgenic mouse, expression of luciferase at the same time in all tissues that express oestrogen receptor is observable or measurable in vivo by non-invasive imaging; and wherein the tissues that express luciferase are uterus, liver, spleen, lung, heart, kidney, hypothalamus and brain.

4. The transgenic mouse according to claim 3, wherein the transgenic mouse is produced by:
   (a) incorporating said reporter transgene into the genome of said mouse by injection of the promoter-reporter construct into fertilized eggs of a mouse whose genome does not include said reporter transgene; and
   (b) obtaining the transgenic mouse that include said reporter transgene in each cell.

5. A cell isolated from the transgenic mouse of claim 3.

6. A transgenic mouse whose genome comprises a transgene comprising a reporter transgene operatively ligated to a constitutive non tissue-specific promoter containing one or more intracellular receptor/transcription factor responsive elements; said promoter-reporter construct being MAR(matrix attachment regions)-ERE(oestrogen receptor responsive element)2X-TKpr(thymidine kinase promoter)-the reporter transgene-MAR or HS4(beta-globin hypersensitive site 4)-ERE2X-TKpr-the reporter transgene-HS4, wherein, when 17-beta estradiol is administered to the transgenic mouse, expression of the reporter transgene at the same time in all tissues that express oestrogen receptor is observable or measurable in vivo by non-invasive imaging; and wherein the tissues that express the reporter transgene are uterus, liver, spleen, lung, heart, kidney, hypothalamus and brain.

7. The transgenic mouse according to claim 6, wherein said reporter transgene is selected from the group consisting of: green fluorescent protein (GFP), beta-galactosidase, beta-lactamase, chloramphenicol acetyltransferase (CAT), dopamine 2 receptor (D2R) and thymidine kinase (TK).

8. The transgenic mouse according to claim 6, wherein the transgenic mouse is produced by:
   (a) incorporating said reporter transgene into the genome of said mouse by injection of the promoter-reporter construct into fertilized eggs of a mouse whose genome does not include said reporter transgene; and
   (b) obtaining the transgenic mouse that include said reporter transgene in each cell.

9. A cell isolated from the transgenic mouse of claim 6.

* * * * *